US00PP32432P2

(12) United States Plant Patent
Fernandez et al.

(10) Patent No.: US PP32,432 P2
(45) Date of Patent: Nov. 10, 2020

(54) STRAWBERRY PLANT NAMED 'NCS 10-156'

(50) Latin Name: ***Fragaria* x *ananassa* Duchense**
Varietal Denomination: NCS 10-156

(71) Applicant: North Carolina State University, Raleigh, NC (US)

(72) Inventors: Gina E. Fernandez, Raleigh, NC (US); Jeremy Pattison, Raleigh, NC (US); James R. Ballington, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 16/602,017

(22) Filed: Jul. 19, 2019

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./156, 208, 209
See application file for complete search history.

(56) References Cited

PUBLICATIONS

NC State Extension website (https://strawberries.ces.ncsu.edu/2016/11/see-nc-state-university-breeding-lines-at-expo-field-tour/). 2020. 8 pages. (Year: 2020).*

Perkins et al. 2016. "Fruit Quality and Composition of Two Advanced North Carolina Strawberry Selections," International Journal of Fruit Science, 16:(Sup 1) 220-227. (Year: 2016).*

Fernandez et al. Breeding Strawberries for North Carolina and the Southern US. The Strawberry Grower, pp. 4-5 Mar. 2015.

Fernandez et al., NC State University Strawberry Breeding Program: Southeast Regional Fruit and Vegetable Conference, Jan. 2017, 54 pages.

Fernandez et al., NC State University Strawberry Breeding Program2015 Yield Trials, Future Projects and Grower Feedback, 121 pages.

Fernandez et al., NC State University Strawberry Breeding Program2015-16 Yield Trials, Grower Feedback and Future Research, 2016, 73 pages.

Fernandez et al., Promising new selections in the NC State University Strawberry Breeding Program, Expo 2014, 43 pages.

Fernandez et al., Promising new selections in the NC State University Strawberry Breeding Program, Strawberry presentation Clemson 2015, 32 pages.

Fernandez, Gina, NC State University Strawberry Breeding Program Update, Nov. 2017, 36 pages.

Fernandez, Gina, Strawberry Grower, North Carolina Strawberry Association, Apr. 2016, 16 pages.

* cited by examiner

*Primary Examiner* — Susan McCormick Ewoldt
*Assistant Examiner* — Karen M Redden
(74) *Attorney, Agent, or Firm* — Myers Bigel, P.A.

(57) ABSTRACT

A new and distinct variety of commercial strawberry plant (*Fragaria* x *ananassa* Duchense) named 'NCS 10-156' substantially as illustrated and described, characterized by its early season of ripening, medium size, excellent flavor, very attractive conical shape with good quality fruit that has soft flesh firmness and soft skin toughness.

4 Drawing Sheets

Latin name of the genus and species: The Latin name of the novel strawberry plant disclosed herein is *Fragaria* x *ananassa* Duchense.

Variety denomination: The inventive strawberry variety has been given the variety denomination 'NCS 10-156'.

BACKGROUND OF THE INVENTION

The present invention relates to a new and distinct variety of strawberry (*Fragaria* x *ananassa* Duchense) named 'NCS 10-156'. This strawberry plant (genotype) originated in a strawberry breeding plot in Salisbury, N.C. The genotype was collected from open pollinated fruit from the seed parent 'NCH 05-73P'. The seed parent is an unreleased breeding selection from a cross that was made to improve the university's strawberry breeding program genepool. The seeds collected from the female parent in the spring of 2009 were germinated in the summer and planted in the fall of 2009. The selection was made in the spring of 2010. 'NCS 10-156' was first asexually propagated at the Piedmont Research Station, Salisbury N.C., Rowan County, in 2011. Ten daughter plants were propagated from runner tips originating from the mother plant and transplanted to second test trials where they were compared to several other genotypes in 2011. Plants were established in replicated trials in 2012-17. 'NCS 10-156' exhibited early fruit production with excellent taste in multiple locations and years. Propagules of 'NCS 10-156' in all trials have been identical to the initial daughter plants. The combination of traits disclosed herein that characterize 'NCS 10-156' have been retained true to type through successive cycles of asexual propagation.

SUMMARY OF THE INVENTION

'NCS 10-156' when grown in the piedmont regions of North Carolina consistently produced fruit early in the season with excellent flavor (Tables 1 and 2, FIG. 3). Yields of NCS 10-156 are higher than 'Sweet Charlie' (U.S. Plant Pat. No. 8,729), the standard early producing cultivar in North Carolina. Fruit of 'NCS 10-156' has higher soluble solids than 'Camarosa' (U.S. Plant Pat. No. 8,708) and 'Chandler' (U.S. Plant Pat. No. 5,262), which gives it a very sweet flavor. 'Sweet Charlie', 'Camarosa' and 'Chandler' are the most commonly planted standard cultivars used by the strawberry industry in North Carolina at this time. 'NCS 10-156' is considered a short day plant which means flowering occurs one time during the season. 'NCS 10-156' begins to flower during week 9-10 and fruit ripening begins week 14-15, the duration of the flowering and fruiting periods are 4 to 8 weeks depending on the season. Preferred planting date is 25 September in Salisbury, N.C. and 5 October in Clayton, N.C. The shelf life of 'NCS 10-156' is short, therefore it is suitable for pick your own and local markets. Nursery performance has been very good in western NC locations due to abundant production of many runners that produce multiple daughter plants that root easily. Yield data of the parents of 'NCS 10-156' is not available. The new and distinct variety of strawberry *Fragaria* x *ananassa* Duchense 'NCS 10-156' has the following unique combination of desirable features that are outstanding in a new variety including (1) early ripening, (2) yields higher than the current early season cultivar 'Sweet Charlie', and (4) excellent flavor.

BRIEF DESCRIPTION OF THE DRAWINGS

The accompanying photographs show typical specimens of 'NCS10-156'. The photographs were taken in Clayton, N.C.

DETAILED BOTANICAL DESCRIPTION

Figure 1:
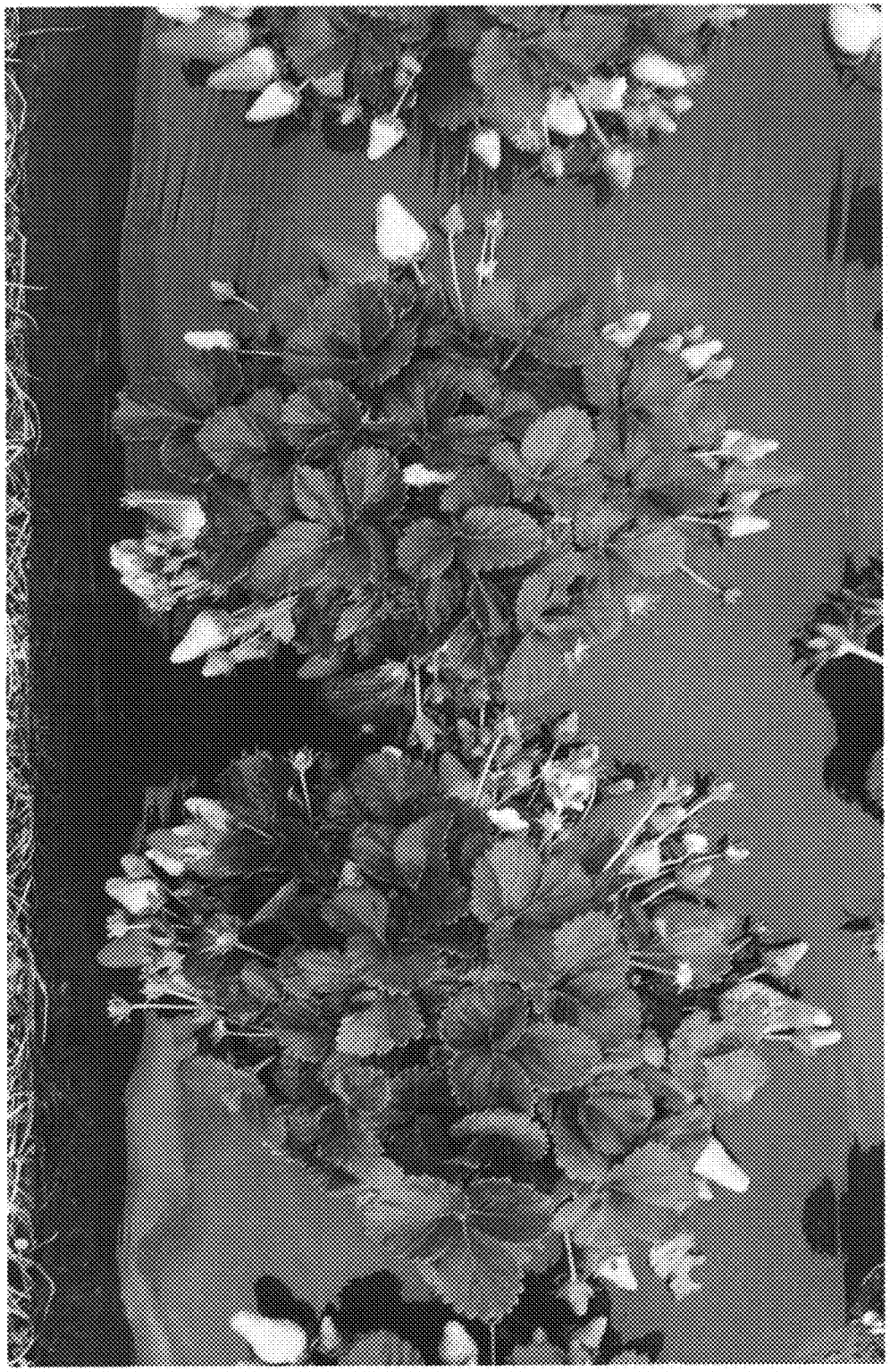
FIG. 1 shows whole 8-month old plants of 'NCS 10-156' including leaves, inflorescences and fruit at varying stages of ripeness.
Figure 2:
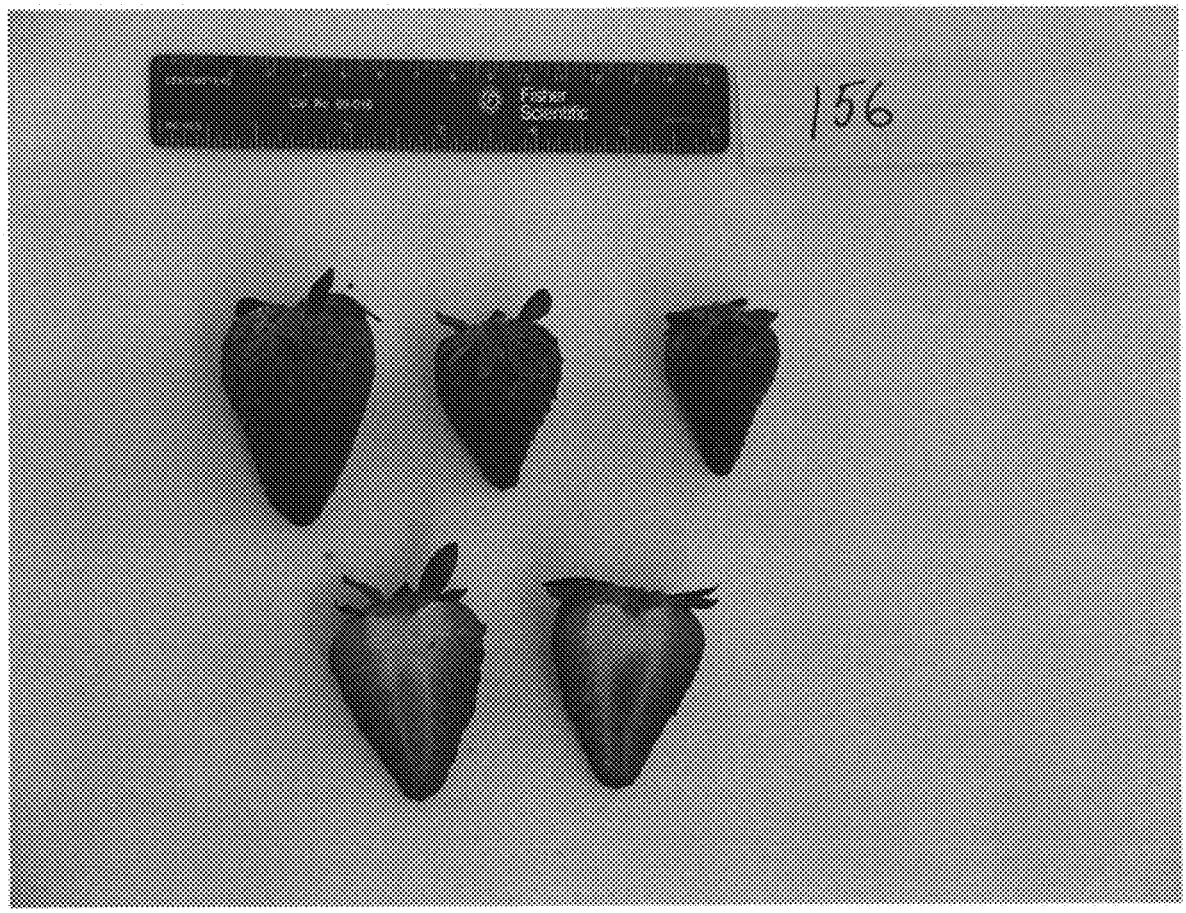
FIG. 2 shows a close up of fruit of 'NCS 10-156', sliced and whole.
Figure 3:
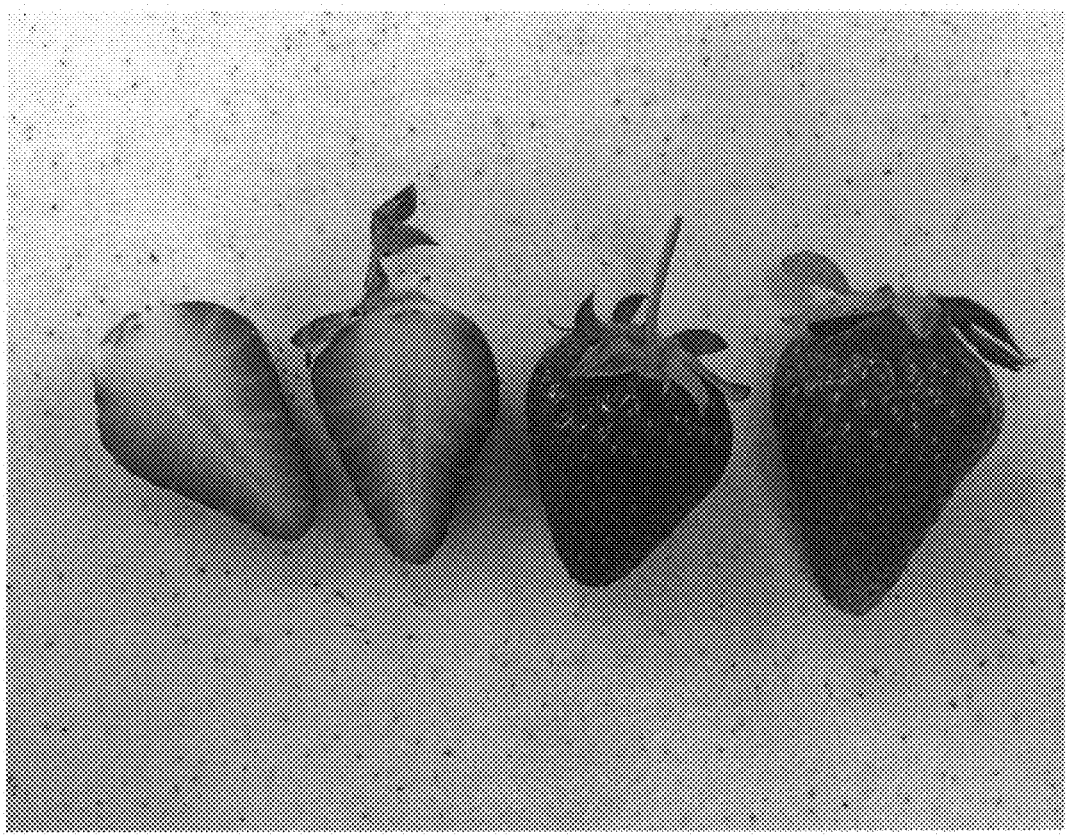
FIG. 3 shows a close-up of fruit of 'NCS 10-156', sliced and whole.

The following is a detailed description of a new distinct strawberry variety known as 'NCS 10-156'. The description is based on observations taken from the 2014-2017 growing seasons in Clayton, N.C. and Salisbury, N.C. The plants are set in the fall and fruiting occurs in the following spring. This description is in accordance with International Union for the Protection of New Varieties of Plants (UPOV) terminology. Color designations and descriptions and other phenotypical traits may deviate from the stated values depending on location and season as this genotype has not been observed in all environmental conditions. Color terminologies are based on The Royal Horticultural Society Colour Chart, London (R.H.S.) ($5^{th}$ Edition. 2007).

Plant:
- *Average height.*—20 cm.
- *Average width.*—15 cm.
- *Canopy density.*—Moderately dense.
- *Growth habit.*—Semi erect moderate compact.
- *Number of crowns/plant.*—3-6.
- *Vigor.*—Moderate.

Leaf:
- *Overall.*—Pinnately compound with 3 leaflets.
- *Mean leaf length including petiole.*—283 mm.
- *Wide.*—151 mm.
- *Terminal leaflet length.*—78 mm.
- *Terminal leaflet width.*—60 mm.
- *Petiole length.*—205 mm.
- *Secondary leaflet length.*—78 mm.
- *Secondary leaflet width.*—55 mm.

Terminal leaflet:
- *Upper leaf surface color.*—137A.
- *Lower leaf surface color.*—138B.
- *Terminal leaflet length.*—7.7 mm.
- *Terminal leaflet width.*—7.5 mm.
- *Length to width ratio.*—1.02.
- *Shape in cross section.*—Concave.
- *Terminal leaflet serration number.*—16-20.
- *Terminal leaflet margin profile.*—Obtuse.
- *Terminal leaflet shape overall.*—Orbicular.
- *Terminal leaflet shape of base.*—Cuneate.
- *Terminal leaflet shape of serrations.*—Pointed.
- *Interveinal blistering.*—Slight.
- *Pubescence density of lower surface.*—Sparse.
- *Leaf glossiness.*—Semi-gloss.
- *Venation pattern.*—Pinnate.

Petiole:
- *Petiole length.*—17.2 mm.
- *Petiole diameter.*—3 mm.
- *Pubescence density of petiole.*—Slight-moderate.
- *Petiole pose of hairs.*—Erect, perpendicular.
- *Petiole color.*—144B.
- *Anthocyanin.*—Absent.

Petiolule:
- *Length.*—Terminal leaflet, 6 mm; lateral leaflet, 6 mm, diameter, 2 mm.
- *Color.*—144B.

Stipule:
- *Stipule length.*—26.8 mm.
- *Stipule width.*—7.5 mm.
- *Stipule color.*—145B.
- *Stipule pubescence.*—Present.
- *Anthocyanin.*—Slight.
- *Bract pair or single.*—Mostly single occasionally paired.

Secondary leaflets:
- *Color upper surface.*—137A.
- *Color lower surface.*—138B.
- *Secondary leaflet length.*—7.7 cm.
- *Secondary leaflet width.*—7.5 cm.
- *Length to width ratio.*—1.02.
- *Shape in cross section.*—Concave.
- *Leaflet shape.*—Orbicular.
- *Leaflet glossiness.*—Glossy.
- *Secondary leaflet serration number.*—14-18.
- *Secondary leaflet margin profile.*—Obtuse.
- *Secondary leaflet shape of base.*—Cuneate to slightly rounded.
- *Secondary leaflet shape of serrations.*—Pointed.
- *Interveinal blistering.*—Moderate.
- *Pubescence density.*—Lower surface — Sparse.
- *Leaf glossiness.*—Semi-gloss.
- *Venation pattern.*—Pinnate.

Stolons:
- *Number of daughter plants.*—25-40 depending on environmental conditions.
- *Anthocyanin.*—Variable, absent to moderate.
- *Thickness.*—3 mm.
- *Pubescence.*—Very sparse nearly glabrous.
- *Average length.*—452 mm.

Inflorescence:
- *Time of flowering.*—Short day flowering habit.
- *Position relative to canopy.*—Flowers open at or below canopy.

*Branching of the inflorescence.*—At or close to crown.
*Number of flowers/inflorescence.*—5.3.
*Relative flower size.*—Medium.
*Relative calyx size to corolla.*—0.78.
*Inflorescence attitude at harvest.*—Level to erect.
*Inflorescence length.*—18-20 mm.
*Flower diameter.*—35 mm primary, 25 mm secondary.
*Calyx diameter.*—26 mm.
*Blossom longevity.*—1-2 days.
*Number of stamens.*—Average of 27.
*Anther color.*—13A to 16A.
*Filament color.*—149D to 150C.
*Style color.*—149D.
*Stigma color.*—2C.

Petals:
*Petal length.*—13.5 mm.
*Petal width.*—14.2 mm.
*Petal size ratio.*—0.95
*Petals/flower.*—5.
*Petal color.*—155D.
*Corolla diameter (mean diameter of the petals collectively).*—33.3 mm.
*Flower shape.*—Orbicular
*Number flowers/inflorescence.*—3-6.
*Petal spacing.*—Even to overlapping.

Sepals:
*Sepal number.*—10.5.
*Sepal color.*—137A.
*Sepal length.*—11.1 mm.
*Sepal width.*—4.2 mm.

Calyx:
*Calyx color.*—N137A tip, N139 base.
*Corolla diameter.*—33.3 mm.
*Calyx size compared to fruit.*—> or =. The calyx attachment is usually level with the fruit, and the sepal attitude is outward and some upward orientation.

Pedicels:
*Color.*—145A.
*Pubescence.*—Light.
*Number of pedicels attached to the truss.*—3.
*Diameter.*—2 mm.
*Length of pedicel attached to the primary fruit.*—59 mm long. At peak production, the plant will have multiple crowns. Each crown will produce one or more truss and each truss will have pedicels.

Fruit:
*Fruit fragrance.*—Highly fragrant.
*Flavor.*—Sweet, high soluble solids content (SSC), see Table 4.
*Fruit skin color.*—53A.
*Fruit flesh color.*—47A.
*Evenness of color.*—Outside skin even, inside from 47A in the apex gradually changing to NN 155C in the center near the calyx.
*Flesh and skin firmness at full ripe stage.*—Moderately soft (See Table 3).
*Rain damage.*—Slight.
*Fruit size average.*—14.6-19.9 g (see Table 1 and Table 2).
*Fruit shape.*—Conical.
*Fruit length.*—36.4 mm.
*Fruit width.*—31.3 mm.
*Fruit length to width ratio.*—1.16.
*Fruit skin glossiness.*—Uniform glossy.
*Fruit calyx orientation.*—Most flat, sometimes raised up.
*Band without achenes.*—4-8 mm.
*Center cavity size.*—0-6 mm.
*Unevenness of surface.*—Seeds sometimes raised, so surface can be uneven.
*Disease resistance.*—Susceptible to grey mold (*Botrytis cinerea*) and anthracnose fruit rot (*Colletotrichum acutatum*).

Seeds:
*Achene color.*—151A and 53A. Achene color is individually present depending on location on fruit.
*Achene attachment.*—At surface to raised.
*Achene shape.*—Oval.

Figure 4:
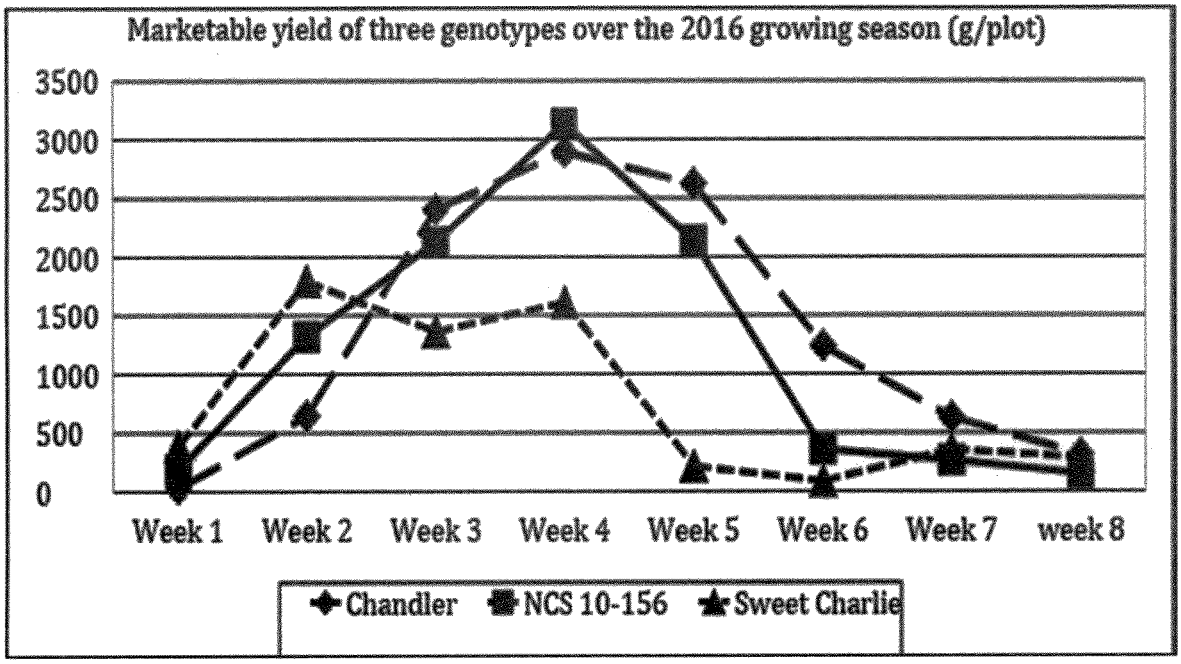
FIG. 4 compares the weekly marketable yield of strawberry varieties 'Chandler', 'NCS 10-156' and 'Sweet Charlie'.

The technical (pomological) descriptive data comparing yield of 'NCS 10-156' to that of 'Sweet Charlie', 'Camarosa' and 'Chandler' in Salisbury, N.C. and in Clayton, N.C. is presented in Tables 1-2. Weekly marketable yield of 'Chandler', 'NCS 10-156' and 'Sweet Charlie' are presented in FIG. 4. Tables 3-4 provide post-harvest storage life attributes comparing 'NCS 10-038' to 'Camarosa' and 'Chandler' as well as 'NCS10-038'. This data was previously published in part in Perkins-Veazie, P., J. Pattison, G. E. Fernandez and G. Ma. 2016. Fruit Quality and Composition of Two Advanced North Carolina Strawberry Selections. *Intl. J. Fruit Science.* 16:(Sup 1): 220-227).

TABLE 1

Piedmont Research Station, Salisbury NC, 2015-16. Total yield, marketable yield, percent marketable yield and average berry weight.

| Genotype | Total Yield (g/plant) | Total Yield (lbs/A) | Marketable Yield (g/plant) | Marketable Yield (lbs/A) |
|---|---|---|---|---|
| NCS 10-038* | 931 | 35749 | 771 | 29605 |
| NCS 10-156 | 697 | 26757 | 586 | 22484 |
| Camarosa | 637 | 24431 | 550 | 21107 |
| Chandler | 665 | 25505 | 505 | 19389 |
| Sweet Charlie | 488 | 18712 | 406 | 15592 |

| Genotype | Percentage Marketable Yield (% of total) | Marketable Percent of Chandler | Average berry weight (g) |
|---|---|---|---|
| NCS 10-038* | 82.8 | 153 | 16.4 |
| NCS 10-156 | 84.0 | 116 | 18.9 |
| Camarosa | 86.4 | 109 | 21.7 |
| Chandler | 76.0 | 100 | 16.9 |
| Sweet Charlie | 83.3 | 80 | 17.3 |

*'NCS 10-038' is co-pending Plant Pat. Application No. 16/602,013

TABLE 2

Central Crops Research Station, Clayton, NC 2015-16. Total yield, marketable yield, percent marketable yield and average berry weight.

| Genotype | Total Yield (g/plant) | Total Yield (lbs/A) | Marketable Yield (g/plant) | Marketable Yield (lbs/A) |
|---|---|---|---|---|
| NCS 10-038* | 785 | 30131 | 712 | 27309 |
| Camarosa | 668 | 25619 | 607 | 23290 |
| Chandler | 669 | 25690 | 539 | 20698 |
| NCS 10-156 | 558 | 21400 | 485 | 18603 |
| Sweet Charlie | 337 | 12941 | 306 | 11725 |

TABLE 2-continued

Central Crops Research Station, Clayton, NC 2015-16. Total yield, marketable yield, percent marketable yield and average berry weight.

| Genotype | Percentage Marketable Yield (% of total) | Marketable Percent of Chandler | Average berry weight (g) |
|---|---|---|---|
| NCS 10-038* | 90.6 | 132 | 17.5 |
| Camarosa | 90.9 | 113 | 18.2 |
| Chandler | 80.6 | 100 | 19.8 |
| NCS 10-156 | 86.9 | 90 | 14.6 |
| Sweet Charlie | 90.6 | 57 | 14.2 |

*'NCS 10-038' is co-pending Plant Pat. Application No. 16/602,013

TABLE 3

Subjective ratings of strawberry fruit held at 4 C for 8 days averaged for 2014 and 2015 seasons[z].

| Selection | Overall appearance[y] | Fruit shrivel | Fruit darkness | Calyx brown | Calyx shrivel | Fruit firmness | Berries with mold (%) |
|---|---|---|---|---|---|---|---|
| Camarosa | 3.8a | 3.9ab | 3.7bc | 3.8a | 3.6a | 4.3a | 3.1a |
| Chandler | 4.0a | 4.3a | 3.8b | 3.9a | 3.8a | 3.2b | 4.6ab |
| NCS 10-038 | 4.0a | 4.4a | 4.2a | 3.4a | 3.6a | 3.8b | 6.1ab |
| NCS 10-156 | 3.3b | 3.3b | 3.2c | 3.0b | 3.0a | 2.2c | 12.3b |

[z]All fruit quality attributes were given subjective ratings of 1 to 5 where a higher number indicates better fruit quality.
Berries with mold was determined by 100% x (no. berries with mold/total no. berries).
[y]Means within column with same letter indicate no significant difference using Tukey's HSD, $p < 0.05$.

TABLE 4

Fruit composition of fully ripe freshly harvested strawberry selections grown at Piedmont, NC in 2014 and 2015[z].

| Selection | SSC (%) | pH | Titratable acidity (TA) (% as citric acid) | SSC/TA | Total anthocyanin (mg P3G/100 g fwt)[y] | Total phenolic content (mg GA/100 g) |
|---|---|---|---|---|---|---|
| Day 0 | | | | | | |
| Camarosa | 7.1b | 3.82a | 0.69b | 10.6ab | 41.27a | 155.62a |
| Chandler | 6.8b | 3.71b | 0.69b | 10.0ab | 48.55a | 157.57a |
| NCS 10-038 | 7.1b | 3.67b | 0.75a | 9.8b | 28.87b | 142.05b |
| NCS 10-156 | 7.8a | 3.78a | 0.72ab | 11.0a | 33.95ab | 152.23a |
| Day 8 | | | | | | |
| Camarosa | 7.6b | 3.97a | 0.64b | 12.1a | 51.52a | 152.16bc |
| Chandler | 7.6b | 3.87b | 0.66b | 11.6a | 45.39ab | 158.50a |
| NCS 10-038 | 6.9c | 3.81b | 0.68b | 10.2b | 29.86c | 147.59c |
| NCS 10-156 | 8.7a | 3.87b | 0.77a | 11.6a | 37.04b | 153.21b |

[z]Each selection consists of a mean of 3 to 7 samples, representing 3 harvest dates per year. Means within column with same letter indicate no significant difference using Tukey's HSD, $p < 0.05$.
[y]P3G and GA are pelargonidin 3-glucoside and gallic acid equivalents, respectively.

That which is claimed is:

1. A new and distinct variety of *Fragaria* x *ananassa* Duch. plant named 'NCS 10-156', substantially as described and illustrated herein.

* * * * *